US012491339B2

(12) United States Patent
Hebert

(10) Patent No.: US 12,491,339 B2
(45) Date of Patent: Dec. 9, 2025

(54) DEVICES FOR STEERING CATHETERS

(71) Applicant: Agile Devices, Inc., Wellesley, MA (US)

(72) Inventor: Stephen J. Hebert, San Francisco, CA (US)

(73) Assignee: Agile Devices, Inc., Wellesley, MA (US)

( * ) Notice: Subject to any disclaimer, the term of this patent is extended or adjusted under 35 U.S.C. 154(b) by 0 days.

(21) Appl. No.: 18/541,017

(22) Filed: Dec. 15, 2023

(65) Prior Publication Data

US 2024/0108859 A1 Apr. 4, 2024

Related U.S. Application Data

(63) Continuation of application No. 17/519,665, filed on Nov. 5, 2021, now Pat. No. 11,872,357.

(60) Provisional application No. 63/111,122, filed on Nov. 9, 2020.

(51) Int. Cl.
*A61M 25/01* (2006.01)
*A61M 25/00* (2006.01)

(52) U.S. Cl.
CPC .... *A61M 25/0133* (2013.01); *A61M 25/0043* (2013.01)

(58) Field of Classification Search
CPC ...................... A61M 25/0133; A61M 25/0138
See application file for complete search history.

(56) References Cited

U.S. PATENT DOCUMENTS

| | | | |
|---|---|---|---|
| 3,521,625 | A | 7/1970 | Mackey |
| 3,791,387 | A | 2/1974 | Itoh |
| 3,903,877 | A | 9/1975 | Terada |
| 4,245,624 | A | 1/1981 | Komiya |
| 4,436,087 | A | 3/1984 | Ouchi |
| 4,548,206 | A | 10/1985 | Osborne |
| 4,699,463 | A | 10/1987 | D'Amelio |
| 4,719,924 | A | 1/1988 | Crittenden |

(Continued)

FOREIGN PATENT DOCUMENTS

| | | |
|---|---|---|
| CN | 10143346905/2009 | 5/2009 |
| EP | 134674709/2003 | 9/2003 |

(Continued)

OTHER PUBLICATIONS

European Search Report EP 21890106 dated Mar. 25, 2024.

(Continued)

*Primary Examiner* — Laura A Bouchelle
(74) *Attorney, Agent, or Firm* — Neil D. Gershon

(57) ABSTRACT

A system including an outer member, an elongated column member extending distally from the outer member and an inner member positioned coaxial with the outer member and attached to the column member. The inner member extends distally of the outer member and has a distal portion. The catheter is positioned within an outer catheter, such as an aspiration catheter, which provides a reinforcement member over the column member to restrict movement of the column member such that when one of the inner member or outer member is moved with respect to the other, axial compression of the column member is restricted by the inner wall of the outer catheter causing the distal portion of the inner member to deflect laterally to thereby redirect the outer catheter.

15 Claims, 10 Drawing Sheets

(56) References Cited

U.S. PATENT DOCUMENTS

| | | | |
|---|---|---|---|
| 4,723,936 | A | 2/1988 | Buchbinder et al. |
| 4,739,786 | A | 4/1988 | Parkinson |
| 4,796,627 | A | 1/1989 | Tucker |
| 4,832,027 | A | 5/1989 | Utz |
| 4,878,485 | A | 11/1989 | Adair |
| 4,927,413 | A | 5/1990 | Hess |
| 4,940,062 | A | 7/1990 | Hampton et al. |
| 4,960,134 | A | 10/1990 | Webster, Jr. |
| 5,010,876 | A | 4/1991 | Henley |
| 5,040,543 | A | 8/1991 | Badera |
| 5,060,660 | A | 10/1991 | Gambale |
| 5,152,744 | A | 10/1992 | Krause |
| 5,168,864 | A | 12/1992 | Dhockey |
| 5,169,568 | A | 12/1992 | Ainger, III |
| 5,199,417 | A | 4/1993 | Mueller et al. |
| 5,222,949 | A | 6/1993 | Kaldany |
| 5,257,617 | A | 11/1993 | Takahashi |
| 5,325,845 | A | 7/1994 | Adair |
| 5,381,782 | A | 1/1995 | DeLaRama |
| 5,383,923 | A | 1/1995 | Webster, Jr. |
| 5,396,880 | A | 3/1995 | Kagan |
| 5,431,168 | A | 7/1995 | Webster, Jr. |
| 5,441,483 | A | 8/1995 | Avitall |
| 5,470,330 | A | 11/1995 | Goldenberg et al. |
| 5,480,382 | A | 1/1996 | Hammerslag |
| 5,484,433 | A | 1/1996 | Taylor et al. |
| 5,562,619 | A | 10/1996 | Mirarchi et al. |
| 5,599,326 | A | 2/1997 | Carter |
| 5,611,777 | A | 3/1997 | Bowden et al. |
| 5,632,734 | A | 5/1997 | Galel et al. |
| 5,702,347 | A | 12/1997 | Yabe |
| 5,711,756 | A | 1/1998 | Chikama |
| 5,715,832 | A | 2/1998 | Koblish et al. |
| 5,779,720 | A | 7/1998 | Walder-Utz et al. |
| 5,820,592 | A | 10/1998 | Hammerslag |
| 5,853,368 | A | 12/1998 | Solomon |
| 5,921,978 | A | 7/1999 | Thompson et al. |
| 5,989,185 | A | 11/1999 | Miyazaki |
| 6,013,024 | A | 1/2000 | Mitsuda |
| 6,059,769 | A | 5/2000 | Lunn et al. |
| 6,083,222 | A | 7/2000 | Klein et al. |
| 6,086,528 | A | 7/2000 | Adair |
| 6,092,526 | A | 7/2000 | LaFointaine et al. |
| 6,096,022 | A | 8/2000 | Laymon et al. |
| 6,123,699 | A | 9/2000 | Webster, Jr. |
| 6,126,649 | A | 10/2000 | VanTassel et al. |
| 6,146,339 | A | 11/2000 | Biagtan |
| 6,200,315 | B1 | 3/2001 | Gaiser |
| 6,428,520 | B1 | 8/2002 | Lopez et al. |
| 6,493,575 | B1 | 12/2002 | Kesten et al. |
| 6,500,167 | B1 | 12/2002 | Webster, Jr. |
| 6,527,769 | B2 | 3/2003 | Langberg et al. |
| 6,554,794 | B1 | 4/2003 | Mueller et al. |
| 6,572,593 | B1 | 6/2003 | Daum |
| 6,591,472 | B1 | 7/2003 | Noone et al. |
| 6,592,581 | B2 | 7/2003 | Bowe |
| 6,640,120 | B1 | 10/2003 | Swanson et al. |
| 6,671,550 | B2 | 12/2003 | Iaizzo et al. |
| 6,726,700 | B1 | 4/2004 | Levine |
| 6,733,500 | B2 | 5/2004 | Kelley et al. |
| 6,743,227 | B2 | 6/2004 | Seraj et al. |
| 6,777,644 | B2 | 8/2004 | Peacock, III |
| 6,778,846 | B1 | 8/2004 | Martinez et al. |
| 6,836,687 | B2 | 12/2004 | Kelley et al. |
| 6,849,078 | B2 | 2/2005 | Durgin et al. |
| 6,893,436 | B2 | 5/2005 | Woodard et al. |
| 6,926,711 | B2 | 8/2005 | Lentz et al. |
| 6,936,047 | B2 | 8/2005 | Nasab et al. |
| 6,951,554 | B2 | 10/2005 | Johansen et al. |
| 7,027,851 | B2 | 4/2006 | Meija |
| 7,039,450 | B2 | 5/2006 | Duarte |
| 7,089,063 | B2 | 8/2006 | Lesh et al. |
| 7,099,717 | B2 | 8/2006 | Woodard et al. |
| 7,252,664 | B2 | 8/2007 | Nasab et al. |
| 7,481,778 | B2 | 1/2009 | Cedro et al. |
| 7,497,844 | B2 | 3/2009 | Spear et al. |
| 7,507,205 | B2 | 3/2009 | Borovsky et al. |
| 7,565,208 | B2 | 7/2009 | Harris et al. |
| 7,569,626 | B2 | 8/2009 | Truckai et al. |
| 7,591,813 | B2 | 9/2009 | Levine et al. |
| 7,615,032 | B2 | 11/2009 | Whittaker et al. |
| 7,615,044 | B2 | 11/2009 | Scheibe et al. |
| 7,641,480 | B1 | 1/2010 | Hossack et al. |
| 7,648,517 | B2 | 1/2010 | Makaower et al. |
| 7,674,253 | B2 | 3/2010 | Fisher et al. |
| 7,694,683 | B2 | 4/2010 | Callister et al. |
| 7,699,829 | B2 | 4/2010 | Harris et al. |
| 7,717,853 | B2 | 5/2010 | Nita |
| 7,731,681 | B2 | 6/2010 | Schaer et al. |
| 7,736,346 | B2 | 6/2010 | Miller et al. |
| 7,766,868 | B2 | 8/2010 | Goode et al. |
| 7,766,961 | B2 | 8/2010 | Patel et al. |
| 7,771,388 | B2 | 8/2010 | Olsen et al. |
| 7,794,454 | B2 | 9/2010 | Abboud et al. |
| 7,815,577 | B2 | 10/2010 | Krishnan |
| 7,818,040 | B2 | 10/2010 | Spear et al. |
| 7,824,517 | B2 | 11/2010 | Kampa et al. |
| 7,867,194 | B2 | 1/2011 | Fiering et al. |
| 7,881,769 | B2 | 2/2011 | Sobe |
| 7,909,797 | B2 | 3/2011 | Kennedy, II et al. |
| 7,914,503 | B2 | 3/2011 | Goodson, IV et al. |
| 7,918,819 | B2 | 4/2011 | Karmarkar et al. |
| 7,922,650 | B2 | 4/2011 | McWeeney et al. |
| 7,922,654 | B2 | 4/2011 | Boutillette et al. |
| 7,942,850 | B2 | 5/2011 | Levit et al. |
| 7,967,830 | B2 | 6/2011 | Ayala et al. |
| 7,976,528 | B2 | 7/2011 | Nash et al. |
| 7,988,646 | B2 | 8/2011 | Tabar |
| 7,998,112 | B2 | 8/2011 | Chow |
| 8,075,498 | B2 | 12/2011 | Leo et al. |
| 8,118,803 | B1 | 2/2012 | Chow et al. |
| 8,147,481 | B2 | 4/2012 | Whittaker et al. |
| 8,147,502 | B2 | 4/2012 | Albrecht |
| 8,152,799 | B2 | 4/2012 | Ormsby et al. |
| 8,172,828 | B2 | 5/2012 | Chang et al. |
| 8,172,829 | B2 | 5/2012 | Farnholtz |
| 8,182,422 | B2 | 5/2012 | Bayer |
| 8,187,286 | B2 | 5/2012 | Jugenheimer et al. |
| 8,195,297 | B2 | 6/2012 | Penner |
| 8,206,320 | B2 | 6/2012 | Deal et al. |
| 8,211,011 | B2 | 7/2012 | Whayne et al. |
| 8,211,087 | B2 | 7/2012 | Carter et al. |
| 8,211,171 | B2 | 7/2012 | Kim et al. |
| 8,213,075 | B2 | 7/2012 | Chui et al. |
| 8,214,018 | B2 | 7/2012 | Markowitz et al. |
| 8,216,224 | B2 | 7/2012 | Morris et al. |
| 8,216,256 | B2 | 7/2012 | Raschdorf, Jr. et al. |
| 8,216,277 | B2 | 7/2012 | Zucherman et al. |
| 8,216,281 | B2 | 7/2012 | Winslow et al. |
| 8,220,466 | B2 | 7/2012 | Frazier et al. |
| 8,220,487 | B2 | 7/2012 | Unger et al. |
| 8,220,494 | B2 | 7/2012 | Struder et al. |
| 8,221,396 | B2 | 7/2012 | Dehnad et al. |
| 8,221,402 | B2 | 7/2012 | Francischelli et al. |
| 8,221,463 | B2 | 7/2012 | Zucherman et al. |
| 8,222,023 | B2 | 7/2012 | Battrell et al. |
| 8,224,422 | B2 | 7/2012 | Mottola et al. |
| 8,224,438 | B2 | 7/2012 | Levin |
| 8,226,246 | B2 | 7/2012 | Shirai et al. |
| 8,228,593 | B2 | 7/2012 | Shirai et al. |
| 8,228,594 | B2 | 7/2012 | Shirai et al. |
| 8,231,613 | B2 | 7/2012 | Baxter et al. |
| 8,231,639 | B2 | 7/2012 | Bolduc et al. |
| 8,234,824 | B2 | 8/2012 | Botkin et al. |
| 8,235,047 | B2 | 8/2012 | Swann et al. |
| 8,235,468 | B2 | 8/2012 | Fookes et al. |
| 8,235,997 | B2 | 8/2012 | Hoffman et al. |
| 8,236,033 | B2 | 8/2012 | Paul |
| 8,238,013 | B2 | 8/2012 | Ichikawa et al. |
| 8,238,019 | B2 | 8/2012 | Endo et al. |
| 8,239,001 | B2 | 8/2012 | Verard et al. |
| 8,241,494 | B2 | 8/2012 | Assion |
| 8,247,178 | B2 | 8/2012 | McBride et al. |
| 8,256,585 | B2 | 9/2012 | Halford et al. |

(56) References Cited

U.S. PATENT DOCUMENTS

| | | | |
|---|---|---|---|
| 8,256,628 | B2 | 9/2012 | Stafford et al. |
| 8,257,369 | B2 | 9/2012 | Gellman et al. |
| 8,257,397 | B2 | 9/2012 | Winslow et al. |
| 8,260,399 | B2 | 9/2012 | Karmarker et al. |
| 8,267,979 | B2 | 9/2012 | Flynn et al. |
| 8,268,446 | B2 | 9/2012 | Desimone et al. |
| 8,270,061 | B2 | 9/2012 | Endo et al. |
| 8,271,069 | B2 | 9/2012 | Jascob et al. |
| 8,273,073 | B2 | 9/2012 | Levine et al. |
| 8,273,086 | B2 | 9/2012 | Serhan et al. |
| 8,273,107 | B2 | 9/2012 | Zucherman et al. |
| 8,273,241 | B2 | 9/2012 | Feldman et al. |
| 8,273,574 | B2 | 9/2012 | Quake et al. |
| 8,323,241 | B2 | 12/2012 | Salahieh et al. |
| 8,388,572 | B2 | 3/2013 | Olsen et al. |
| 8,684,953 | B2 | 4/2014 | Cabiri |
| 8,740,815 | B2 | 6/2014 | Palme |
| 8,920,369 | B2 | 12/2014 | Salahieh et al. |
| 8,926,588 | B2 | 1/2015 | Berthiaume |
| 9,138,566 | B2 | 9/2015 | Cabiri |
| 9,174,022 | B2 | 11/2015 | Uihlein |
| 9,233,225 | B2 | 1/2016 | Hebert |
| 9,549,666 | B2 | 1/2017 | Herbert |
| 2002/0002329 | A1 | 1/2002 | Avitall |
| 2002/0007110 | A1 | 1/2002 | Irion |
| 2002/0068924 | A1 | 6/2002 | Sinofsky |
| 2002/0072712 | A1 | 6/2002 | Nool et al. |
| 2002/0161330 | A1 | 10/2002 | Nguyen |
| 2003/0114844 | A1 | 6/2003 | Ormsby et al. |
| 2003/0164952 | A1 | 9/2003 | Deichmann |
| 2004/0097804 | A1 | 5/2004 | Sobe |
| 2004/0116851 | A1 | 6/2004 | Johansen et al. |
| 2004/0176741 | A1 | 9/2004 | Famholtz |
| 2004/0225256 | A1 | 11/2004 | Ponzi et al. |
| 2005/0010237 | A1 | 1/2005 | Niazi |
| 2005/0020914 | A1 | 1/2005 | Amundson et al. |
| 2005/0054976 | A1 | 3/2005 | Goode et al. |
| 2005/0065512 | A1 | 3/2005 | Schaer |
| 2005/0070794 | A1 | 3/2005 | Deal et al. |
| 2005/0070821 | A1 | 3/2005 | Deal et al. |
| 2005/0131343 | A1 | 6/2005 | Abrams et al. |
| 2005/0143770 | A1 | 6/2005 | Carter et al. |
| 2005/0177024 | A1 | 8/2005 | Mackin |
| 2005/0187519 | A1 | 8/2005 | Harris et al. |
| 2005/0222557 | A1 | 10/2005 | Baxter et al. |
| 2005/0222558 | A1 | 10/2005 | Baxter et al. |
| 2005/0234436 | A1 | 10/2005 | Baxter et al. |
| 2005/0234437 | A1 | 10/2005 | Baxter et al. |
| 2005/0273020 | A1 | 12/2005 | Whittaker et al. |
| 2005/0277808 | A1 | 12/2005 | Sonnenschein |
| 2006/0025705 | A1 | 2/2006 | Whittaker et al. |
| 2006/0030864 | A1 | 2/2006 | Kennedy, II et al. |
| 2006/0142732 | A1 | 6/2006 | Karmarkar et al. |
| 2006/0167418 | A1 | 7/2006 | Khayal et al. |
| 2006/0241564 | A1 | 10/2006 | Corcoran et al. |
| 2006/0247556 | A1 | 11/2006 | Lupton |
| 2006/0265043 | A1 | 11/2006 | Mandrusov et al. |
| 2006/0282151 | A1 | 12/2006 | Weber |
| 2007/0060847 | A1 | 3/2007 | Leo et al. |
| 2007/0149851 | A1 | 6/2007 | Nakamura |
| 2007/0156114 | A1 | 7/2007 | Worley et al. |
| 2007/0156131 | A1 | 7/2007 | Datta |
| 2007/0156133 | A1 | 7/2007 | McDaniel et al. |
| 2007/0191765 | A1 | 8/2007 | Olsen |
| 2007/0219465 | A1 | 9/2007 | Cedro |
| 2007/0225680 | A1 | 9/2007 | Biggins |
| 2007/0265595 | A1 | 11/2007 | Miyamoto |
| 2007/0282303 | A1 | 12/2007 | Nash et al. |
| 2008/0009745 | A1 | 1/2008 | Hossack et al. |
| 2008/0086047 | A1 | 4/2008 | McDaniel et al. |
| 2008/0097499 | A1 | 4/2008 | Nash et al. |
| 2008/0167524 | A1 | 7/2008 | Goldwasser et al. |
| 2008/0172037 | A1 | 7/2008 | Huang et al. |
| 2008/0208240 | A1 | 8/2008 | Paz |
| 2008/0234547 | A1 | 9/2008 | Irion et al. |
| 2008/0234661 | A1 | 9/2008 | Hastings et al. |
| 2008/0275536 | A1 | 11/2008 | Zarins et al. |
| 2008/0287945 | A1 | 11/2008 | Schaer |
| 2008/0312712 | A1 | 12/2008 | Penner |
| 2008/0312725 | A1 | 12/2008 | Penner |
| 2009/0005754 | A1 | 1/2009 | Soetermans |
| 2009/0043299 | A1 | 2/2009 | Racz |
| 2009/0082723 | A1 | 3/2009 | Krogh |
| 2009/0099420 | A1 | 4/2009 | Woodley |
| 2009/0105814 | A1 | 4/2009 | Groothuis et al. |
| 2009/0105815 | A1 | 4/2009 | Krever et al. |
| 2009/0105816 | A1 | 4/2009 | Olsen et al. |
| 2009/0137953 | A1 | 5/2009 | Fischer et al. |
| 2009/0149848 | A1 | 6/2009 | Werneth et al. |
| 2009/0163822 | A1 | 6/2009 | Doan |
| 2009/0171278 | A1 | 7/2009 | Hirszowicz et al. |
| 2010/0004627 | A1 | 1/2010 | Ludwig et al. |
| 2010/0030114 | A1 | 2/2010 | Nguyen et al. |
| 2010/0036329 | A1 | 2/2010 | Razack |
| 2010/0057037 | A1 | 3/2010 | Webler |
| 2010/0063478 | A1 | 3/2010 | Selkee |
| 2010/0063479 | A1 | 3/2010 | Merdan |
| 2010/0076408 | A1 | 3/2010 | Krever et al. |
| 2010/0094334 | A1 | 4/2010 | Krever et al. |
| 2010/0164137 | A1 | 7/2010 | Selkee |
| 2010/0168666 | A1 | 7/2010 | Tegg |
| 2010/0198049 | A1 | 8/2010 | Karmarkar et al. |
| 2010/0204560 | A1 | 8/2010 | Salahieh et al. |
| 2010/0217261 | A1 | 8/2010 | Watson |
| 2010/0226903 | A1 | 9/2010 | Morris et al. |
| 2010/0280449 | A1 | 11/2010 | Alvarez |
| 2010/0286475 | A1 | 11/2010 | Robertson |
| 2010/0286626 | A1 | 11/2010 | Peterson et al. |
| 2010/0312096 | A1 | 12/2010 | Guttman et al. |
| 2010/0312178 | A1 | 12/2010 | Olsen et al. |
| 2010/0331776 | A1 | 12/2010 | Salahieh |
| 2011/0028826 | A1 | 2/2011 | Kim et al. |
| 2011/0054465 | A1 | 3/2011 | Werneth et al. |
| 2011/0060331 | A1 | 3/2011 | Ibrahim et al. |
| 2011/0087112 | A1 | 4/2011 | Leo et al. |
| 2011/0087175 | A1 | 4/2011 | Krishnan et al. |
| 2011/0130750 | A1 | 6/2011 | Ormsby et al. |
| 2011/0166455 | A1 | 7/2011 | Cully et al. |
| 2011/0166569 | A1 | 7/2011 | Whayne |
| 2011/0190784 | A1 | 8/2011 | Hastings et al. |
| 2011/0213300 | A1 | 9/2011 | McWeeney et al. |
| 2011/0224784 | A1 | 9/2011 | Quinn |
| 2011/0245842 | A1 | 10/2011 | Doan et al. |
| 2011/0251519 | A1 | 10/2011 | Romoscanu |
| 2011/0264011 | A1 | 10/2011 | Wu et al. |
| 2012/0010490 | A1 | 1/2012 | Kauphusman et al. |
| 2012/0046666 | A1 | 2/2012 | Klein |
| 2012/0053419 | A1 | 3/2012 | Bloom |
| 2012/0071870 | A1 | 3/2012 | Salahieh et al. |
| 2012/0109079 | A1 | 5/2012 | Asleson et al. |
| 2012/0111482 | A1 | 5/2012 | Grunewald et al. |
| 2012/0116199 | A1 | 5/2012 | De La Rama et al. |
| 2012/0116200 | A1 | 5/2012 | Roy et al. |
| 2012/0130217 | A1 | 5/2012 | Kauphusman et al. |
| 2012/0130218 | A1 | 5/2012 | Kauphusman et al. |
| 2012/0143099 | A1 | 6/2012 | Daniels et al. |
| 2012/0143177 | A1 | 6/2012 | Avitall |
| 2012/0190927 | A1 | 7/2012 | Uihleim |
| 2012/0203169 | A1 | 8/2012 | Tegg |
| 2012/0209071 | A1 | 8/2012 | Bayer |
| 2012/0232563 | A1 | 9/2012 | Williams et al. |
| 2012/0239002 | A1 | 9/2012 | Griswold |
| 2012/0277730 | A1 | 11/2012 | Salahieh et al. |
| 2013/0030246 | A1 | 1/2013 | Francis |
| 2013/0041214 | A1 | 2/2013 | Maahs |
| 2013/0109919 | A1 | 5/2013 | Sugiyama |
| 2013/0116705 | A1 | 5/2013 | Salahieh et al. |
| 2013/0204096 | A1 | 8/2013 | Ku |
| 2014/0088361 | A1 | 3/2014 | Hrayr |
| 2014/0107623 | A1 | 4/2014 | Salahieh et al. |
| 2015/0173782 | A1 * | 6/2015 | Garrison ........... A61M 25/0043 606/127 |

(56) References Cited

U.S. PATENT DOCUMENTS

| | | | | |
|---|---|---|---|---|
| 2015/0374955 | A1* | 12/2015 | Hebert | A61M 25/09<br>604/95.04 |
| 2020/0196837 | A1 | 6/2020 | Hebert | |
| 2021/0282759 | A1 | 9/2021 | Layman et al. | |

FOREIGN PATENT DOCUMENTS

| | | |
|---|---|---|
| EP | 152589704/2005 | 4/2005 |
| JP | 2010/11970706/2010 | 6/2010 |
| JP | 2015-533622 | 11/2015 |
| JP | 2017-500153 | 1/2017 |
| WO | WO 2011/03378303/2011 | 3/2011 |
| WO | WO 2012/02738303/2012 | 3/2012 |
| WO | WO 2012/09681607/2012 | 7/2012 |

OTHER PUBLICATIONS

PCT/US2021/058156 International Search Report (Jan. 27, 2022).
PCT/US2013/069435 International Search Report (Nov. 11, 2013).
PCT/US2013/069470 International Search Report (Nov. 11, 2013).
The Extended European Search Report Application No. 13853310.4 dated Jul. 1, 2016.

* cited by examiner 409
350
412
322
316a
410
314
314a
300
340

350
316a
412
410
314
340

316a
412
410
340

DEVICES FOR STEERING CATHETERS

This application is a continuation of application Ser. No. 17/519,665, filed Nov. 5, 2021, which claims priority to provisional application 63/111,122, filed Nov. 9, 2020. The entire contents of each of these applications are incorporated herein by reference.

BACKGROUND

Technical Field

This application relates to medical devices, and more particularly, to medical devices for steering catheters to aid passage through tortuous pathways.

Background of Related Art

The necessity for steering catheters through tortuous pathways is widely recognized. There are several approaches to achieving such steerability.

The coaxial catheter disclosed in U.S. Pat. No. 9,233,225 (hereinafter the '225 patent), by the same inventor as the present application, provides a deflectable catheter having a deflection mechanism in the form a column member to deflect the catheter. The column member is attached at one end to the inner catheter and at the other end to the outer catheter. A reinforcement tube is placed over the column member to restrict axial movement of the column member such that when one of the inner catheter or outer catheter is moved with respect to the other, axial compression of the column member is restricted by the reinforcement member causing the distal tip portion of the inner catheter to deflect laterally.

Although the catheter of the '225 patent advantageously achieves deflection in a low profile, less complicated and consistent manner, in certain applications it might be beneficial to further reduce the profile. It also might be beneficial in certain applications to design the column member so it can be used with a variety of catheters.

Current catheters also have difficulty navigating tortuous anatomy, e.g., the anatomy of the neurovasculature, Due to the size difference of certain catheters, such as aspiration catheters, and the smaller diameter guidewire or smaller diameter catheter over which they are inserted, these catheters oftentimes get caught up at vessel junctions, referred to as the ledge effect, and/or the shoulder between the catheter and inner guidewire or inner catheter, can damage the vessel wall and possibly cause a dissection and subarachnoid hemorrhage.

It would be advantageous to provide a system that improves the navigability of catheters through tortuous vasculature and avoids the potential of getting caught on vessel junctions or causing trauma to the vessel. Such systems for certain applications would advantageously have a reduced profile to facilitate crossing of a blood clot.

SUMMARY

The present invention provides a bi-directional deflectable device which provides a low (reduced) profile and enables use with a variety of catheters. Thus, the devices of the present invention can be inserted into standard catheters or uniquely designed catheters and actuated to deflect such catheters, achievable without having to alter the structure of the catheter.

The coaxial bi-directional deflectable devices/systems of the present invention facilitate navigating through the tortuous vasculature and reduce the potential of catheters getting caught at vessel junctions during insertion and reduce the chance of trauma, e.g., reduce the risk of vessel dissection or hemorrhaging, during insertion/navigation.

The present invention provides in one aspect a deflectable device (e.g., a deflectable catheter) that is placed within another independent outer catheter, and utilizing the devices deflection mechanism, i.e., column member, deflects the outer catheter.

The present invention provides in another aspect a system comprising a first device having an outer member having a proximal portion and a distal portion, an inner member positioned coaxially within the outer member and extending distally of the outer member and having a distal portion, and an elongated column member attached to the inner member and extending external of the inner member. The first device is slidably positioned within the lumen of an outer catheter so that the column member is positioned in the lumen of the outer catheter, wherein when one of the inner member or outer member is moved with respect to the other, axial compression of the column member is restricted by an inner wall of the outer catheter causing the distal portion of the inner member to deflect laterally to redirect the outer catheter.

In some embodiments, the inner member has a central longitudinal axis and the column member is radially offset with respect to the central longitudinal axis.

In some embodiments, the outer catheter is an aspiration catheter.

In some embodiments, the column member is non-circular in cross-section.

In some embodiments, a marker band is positioned on the inner member and the column member is attached to the marker band.

In some embodiments, the column member is attached at a proximal end to the outer member and at the distal end to the inner member.

In some embodiments, the column member has a distal terminal end adjacent a softer distal section of the inner member and the inner member extends for a length from about 2 cm from the distal terminal end of the column member.

In some embodiments, the column member has a reinforcement member positioned thereover, the reinforcement member coming into contact with the inner wall of the second catheter during deflection.

In some embodiments, the column member comes into contact with the inner wall of the outer catheter during deflection.

In accordance with another aspect of the present invention, a system is provided comprising a) an outer member having a proximal portion and a distal portion; b) an inner member positioned coaxially within the outer member, the inner member extending distally of the outer member and having a distal portion and a distalmost edge; and c) an elongated column member attached to the inner member and extending external of the inner member. The column member is attached at a first end to the outer member and at a second end to the inner member. The second end of the column member is positioned proximally of the distalmost edge of the inner member to leave an extended elongated portion of the inner member extending distally of the column member. When the column member is restricted by an outer structure, and one of the inner member or outer member is moved with respect to the other, the distal portion of the inner member deflects laterally.

The column member preferably terminates at a distal end adjacent the softer distal section of the inner member.

In some embodiments, lateral deflection is effected when the column member is restricted by an inner wall of an outer catheter in which the column member is positioned.

In some embodiments, a marker band is positioned on the inner member spaced proximally of the distalmost edge or elongated portion, and the column member is attached to the marker band.

In accordance with another aspect of the present invention, a method for directing a catheter through the vasculature is provided comprising:

a) inserting a first device into an outer catheter, the first device having an inner member, an outer member and a column member connected to the inner member and/or outer member;

b) moving one of the inner member or outer member with respect to the other to effect axial compression of the column member as the column member is bent within a lumen of the outer catheter, the inner wall restricting movement of the column member so a distal portion of the inner member deflects laterally; and c) advancing the outer catheter over the deflected distal portion to redirect the outer catheter.

The outer catheter can be advanced independently over the device or advanced as a unit with the device.

In some embodiments, the column member is deflected to contact the inner wall of the outer catheter and provides an anchoring of the first device.

In some embodiments, the outer catheter is an aspiration catheter.

In some embodiments, manipulation of the distal portion of the first device via the column member re-directs the outer catheter away from an ophthalmic artery junction.

In some embodiments, the method further comprises the step of moving the column member to stabilize the exposed section of the inner member.

In some embodiments, the method further comprises advancing a portion of the inner member extending distally of the column member through a blood clot in the vessel. In some embodiments, the method further comprises passing a stentriever or other clot treatment device through the inner member after the inner member portion is passed through the blood clot.

BRIEF DESCRIPTION OF THE DRAWINGS

Preferred embodiments of the present disclosure are described herein with reference to the drawings wherein:

FIGS. 13A-13F illustrate use of the device of FIG. 6 in a procedure to dislodge a blood clot wherein:

FIG. 13A shows crossing of the clot with a guidewire;

FIG. 13B shows the distal end of the device moved distally to cross the clot;

FIG. 13C shows the device in position with the guidewire removed;

FIG. 13D shows deployment of the stentriever through the inner member;

FIG. 13E shows aspiration through the outer catheter; and

FIG. 13F shows movement of the stentriever proximally to remove the clot.

DETAILED DESCRIPTION

Figure 1:
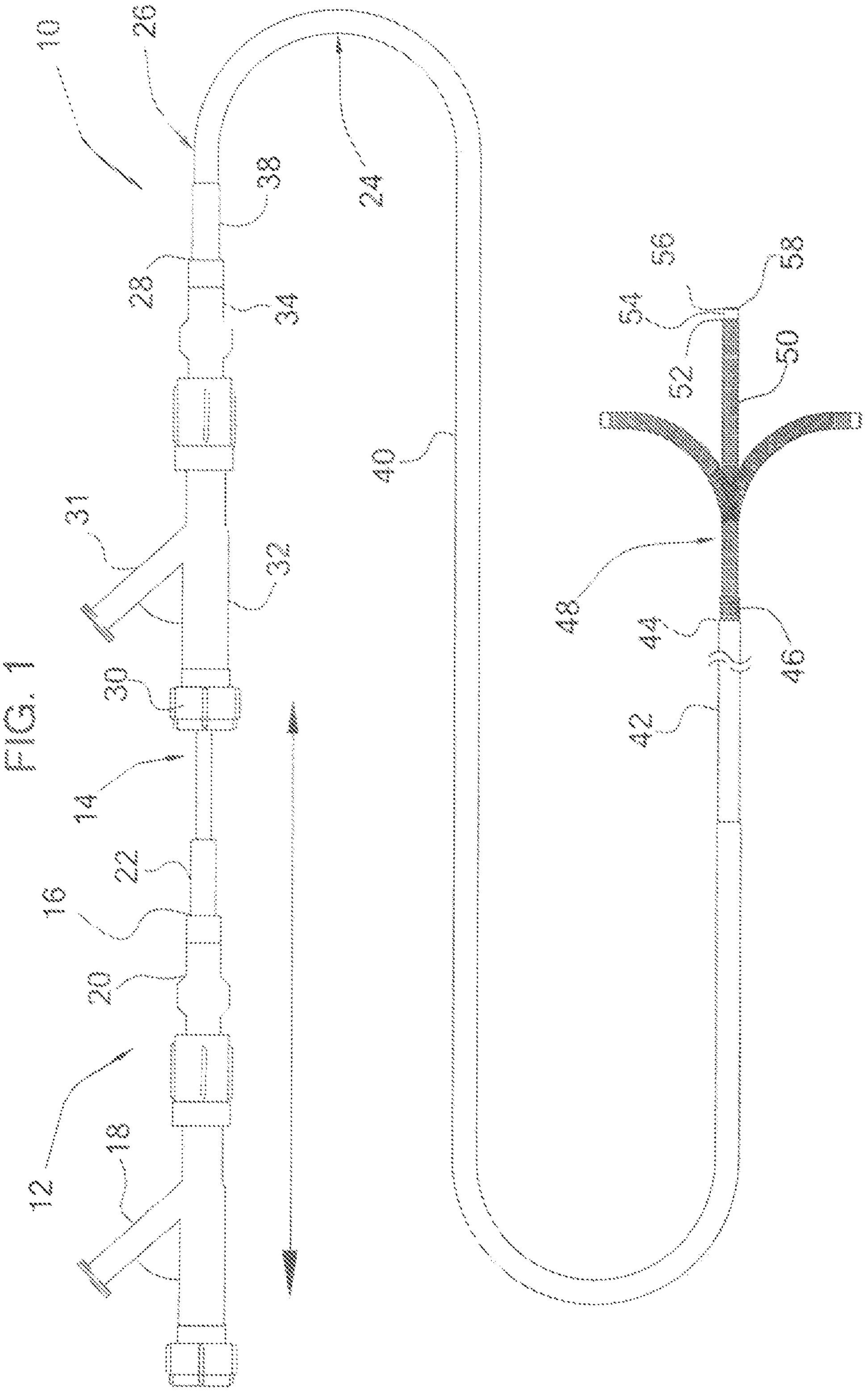
FIG. 1 Prior Art
FIG. 1 is a side view of a deflectable catheter of the prior art disclosed in U.S. Pat. No. 9,233,225.

The present invention provides a bi-directional deflectable device (catheter) with enhanced deflection to enable and facilitate tip deflection in narrow tortuous vasculature. The device has a deflectable distal portion which is deflected due to the arrangement of the inner member, outer member and column member. The column member is attached to the inner member and outer member. The device is insertable into an outer catheter, such as an aspiration catheter, intermediate catheter, or other catheter, so the column member of the device is within the lumen of the outer catheter such that the inner wall of the lumen of the outer catheter provides a movement restriction member of the column member. Relative movement of the outer member and inner member effects lateral deflection of the distal portion of the device due to the restriction member (provided by the outer catheter) limiting axial movement of the column. This is explained in more detail below.

In the devices of the present invention, the column member is spaced proximally a sufficient distance from the distal tip of the inner member. This presents a lower profile to enable for example crossing of a clot. This is also described in more detail below.

U.S. Pat. No. 9,233,225, by the same inventor as the present application, discloses a deflectable catheter having a deflection mechanism in the form of a column member to deflect the catheter. The column member is attached at one end to the inner catheter (member) and at the other end to the outer catheter (member). A reinforcement tube is placed over the column member to restrict axial movement of the column member such that when one of the inner catheter or outer catheter is moved with respect to the other, axial compression of the column member is restricted by the reinforcement member causing the distal tip portion of the inner catheter to deflect laterally.

Although the catheter of the '225 patent advantageously achieves deflection in a low profile, less complicated and consistent manner, in certain applications it might be beneficial to further reduce the profile, such as for crossing a clot. It also might be beneficial in certain applications to design the column member so it can be used with a variety of catheters, i.e., the restriction member is not "built into" the device.

FIGS. 1-5, labeled as "prior art", illustrate features of the catheter of the '225 patent to facilitate understanding of the present invention. FIGS. 1-5 will be described first, followed by a detailed discussion of the devices of the present invention. It should be appreciated that the discussion below of FIGS. 1-5 provides a summary, and further details can be found in U.S. Pat. No. 9,233,225 (hereinafter the '225 patent), the entire contents of which are incorporated herein by reference.

In FIGS. 1-5, the movement restriction (reinforcement) member is part of the catheter, (built into the catheter) to effect deflection of the catheter. In the present invention of FIGS. 6-11, the movement restriction (reinforcement) member is provided by a separate outer catheter in which the device of the present invention is positioned, and the device of the present invention is used to deflect the outer catheter.

Turning to FIG. 1, the bi-directional coaxial deflectable microcatheter of the prior art '225 patent is illustrated. The catheter 10 includes an inner catheter (member) 12, an outer catheter (member) 24 and a distal portion 48 with a deflectable tip.

The inner catheter 12 extends between proximal end 16 and distal end 58 having an inner lumen with a diameter in the range of about 0.001" inches to about 1.993" inches with a preferred inner diameter of about 0.017" inches. Coupled to the proximal end of inner catheter body 14 is winged hub 20 which sits on a strain relief 22. Winged hub 20 can also be fitted with a rotating hemostatic valve (RHV) 18 to provide a channel into the inner lumen of inner catheter 12 for insertion of an accessory or fluid introduction through the side arm.

Inner catheter 12 includes catheter body 14 which has a stiff proximal section made up of a braid reinforced polymer tube extending between proximal end 16 and distalmost end 58. The proximal section is coupled at a distal end to a less stiff distal tube. Inner catheter body 14 further includes a laser cut tube 76 (FIG. 4), which is coupled to the distal tube at its distal end.

One embodiment has a lubricious inner liner that runs from a proximal end to a distal end to help reduce the coefficient of friction to aid in guidewire movement within the inner catheter.

The '225 patent discloses various embodiments of the inner catheter. In these embodiments, the column member extends almost to the end of the inner catheter.

Figure 2:
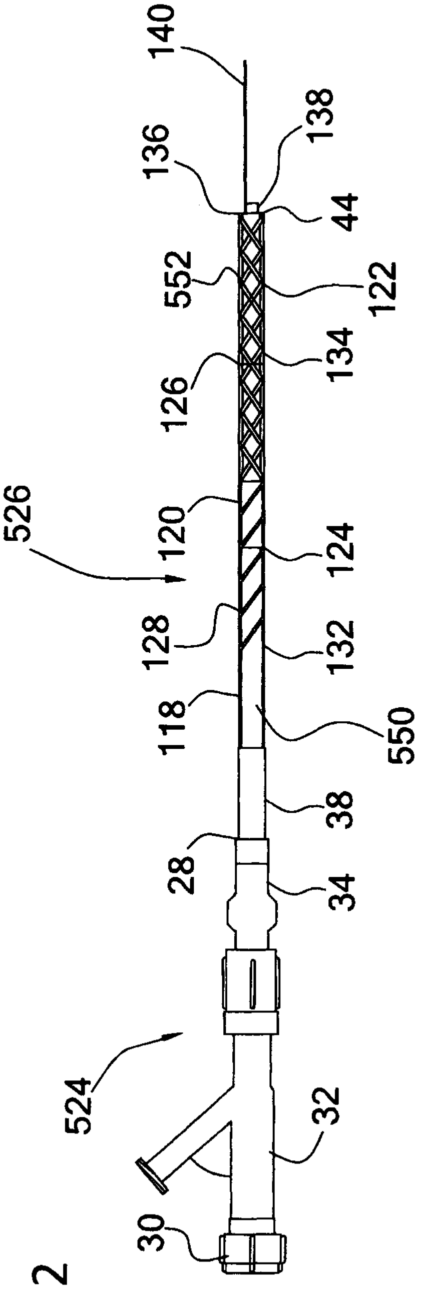
FIG. 2 is a side view of the outer catheter of the prior art of FIG. 1 showing the column member extending therefrom.
Figure 3:
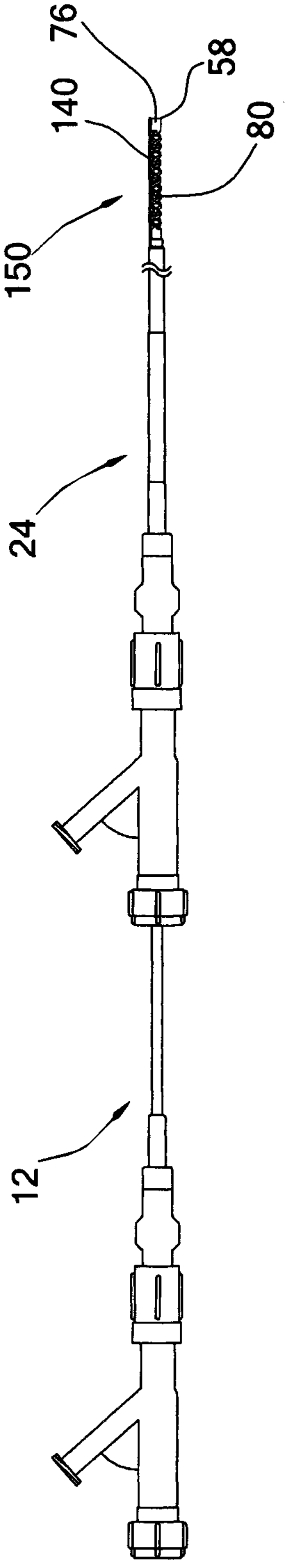
FIG. 3 Prior Art
FIG. 3 is a side view of the inner catheter of the prior art of FIG. 1 within the outer catheter to form the deflectable catheter (the reinforcement tube removed for clarity)

Outer catheter 24 has an inner lumen that extends between proximal end 28 and distal end 44 having a diameter in the range of about 0.007" to about 1.999" with a preferred inner diameter of about 0.027". Outer catheter body 26 has a relatively stiff proximal section 40 that is joined to a relatively flexible distal section 42. Coupled to the proximal end of outer catheter body 26 is winged hub (luer) 34, which sits on strain relief 38 (FIG. 2). Attached to winged hub 20 is rotating hemostatic valve (RHV) 32 with end cap 30 and side arm 31. End (lock) cap 30 acts as the locking assembly for the deflectable catheter while side arm 31 is used for introduction of fluids for lubrication and possibly visualization. When cap 30 is fully opened, inner catheter 12 is free to move axially resulting in distal tip 48 deflection as described below. Cap 30 can be tightened at any point in the deflection process to clamp and hold inner catheter 12 in position and thereby lock the tip 48 in place.

Deflectable tip 48 of inner catheter 12 is covered with lateral support tube 50, which overlies the column member described below. Support tube 50 FIGS. 2 and 5) is adhered at its proximal and distal ends 46 and 52, respectively. Lateral support tube 50 is a helically wound flexible coil. Disposed distally of lateral support tube 50 is a radiopaque marker band 54, which is adhered at end 56 to the distalmost end 58 of the inner catheter 10.

Outer catheter 24 can have a lubricious liner 128 that runs from proximal end 28 to distal end 44 to aid in movement of the inner catheter during the deflection process by reducing the coefficient of friction between the outer catheter inner diameter and the inner catheter outer diameter. The catheter includes a laser cut tube and distal braid. The liner is topped with a reinforcement layer. The reinforcement layer is topped with polymers with varying stiffnesses to create three distinct sections, with stiffness decreasing from proximal section 118 to distal section 122. Outer catheter body 26 includes a marker band 138, which is inserted mid way into the inner diameter at the distal end of outer catheter body 26.

Various embodiments of the outer catheter are disclosed in the '225 patent such as having a continuous open pitch coil.

The catheter 10 includes a column member e.g., a wire or tube, which extends distally of the outer catheter 24 (or 524) and is attached to the inner catheter and is surrounded by a restriction (support) tube to restrict lateral movement of the column member. As shown, the column member includes a column 140, which at its proximal end sits on marker band 138 or in a slot of the marker band 138. The proximal portion of column 140 is inserted into the inner diameter, i.e., the catheter body wall, at the distal end of outer catheter body 26. Column 140 has a substantially rectangular cross section.

Inner catheter 12 and outer catheter 24 are aligned and joined together with marker band 54 and adhesive or solder joint 56 at the distal portion.

Figure 5:
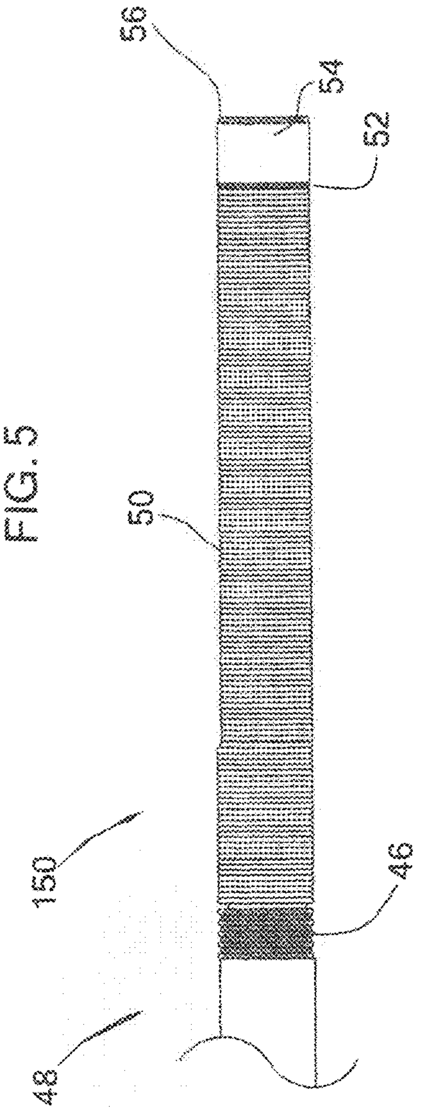
FIG. 5 Prior Art
FIG. 5 is an enlarged view of the distal portion of the deflectable catheter of FIG. 4 with the lateral reinforcement tube.

Alignment of the distal ends of column 140 and the inner catheter 12 (distal ends are approximately flush) is shown in FIG. 5.

Figure 4:
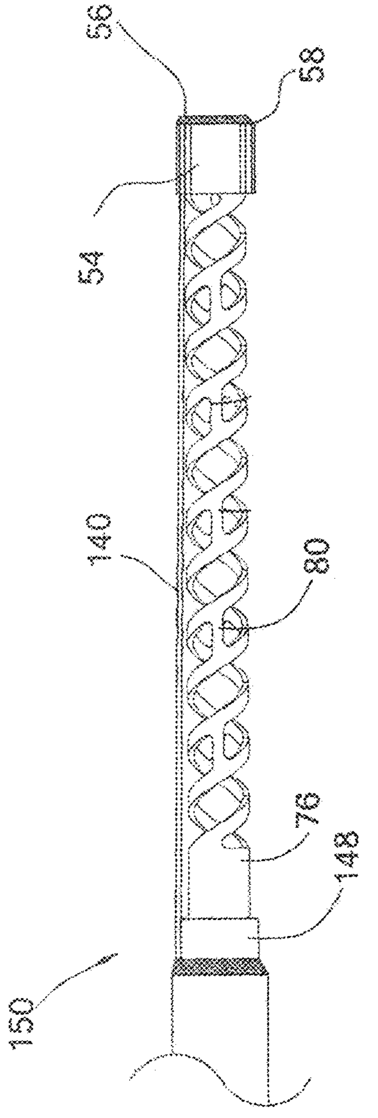
FIG. 4 is an enlarged view of the distal portion of the deflectable catheter of FIG. 3 with the lateral reinforcement (support) tube removed to show the column.

FIG. 5 illustrates distal portion 150 with lateral support tube 50 in place which forms a cover for the column. Lateral support tube 50 is a closed pitch helically wound flexible coil made of platinum/iridium. FIG. 4 shows the distal portion 150 before attachment of the support tube 50.

Figure 12B:
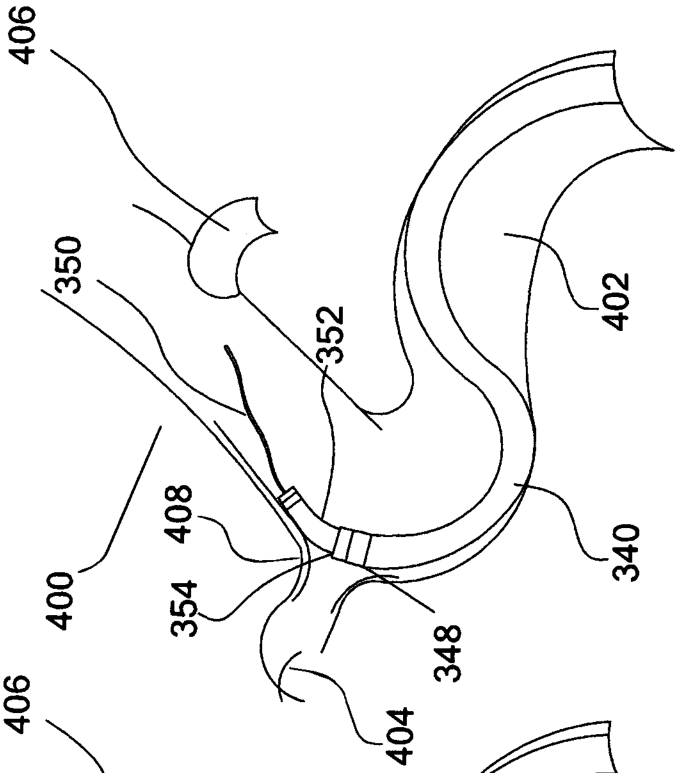
FIG. 12B is a view similar to FIG. 12A showing the aspiration catheter guided by a smaller distal access catheter.
Figure 12A:
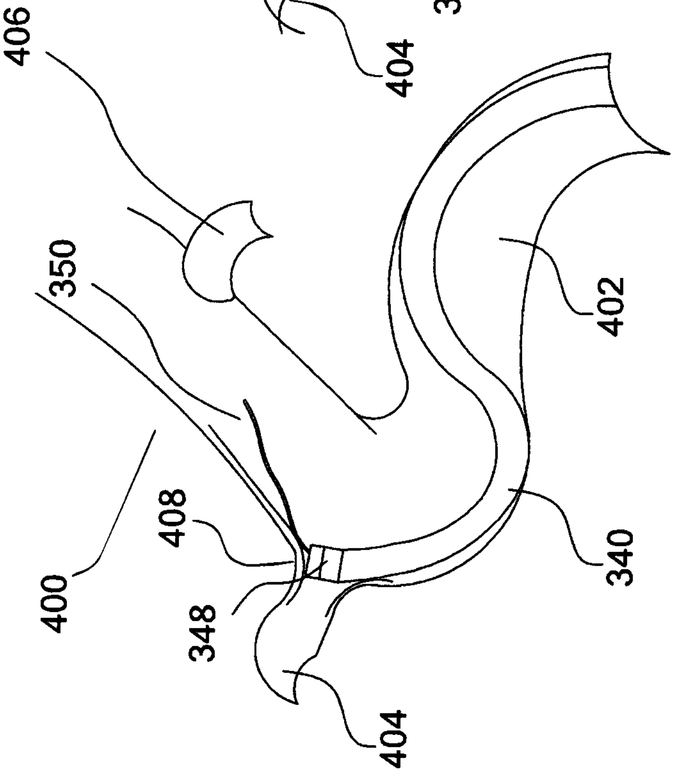
FIG. 12A is a perspective view showing how an aspiration catheter can get caught at the ophthalmic artery junction of the neurovasculature.

FIG. 12A of the '225 patent illustrates the distal portion of the inner catheter under an axial pull load in the absence of the lateral support tube 50. When inner catheter body is pulled axially by a load in the proximal direction, the internal structure will want to shorten causing column 140 to compress. FIG. 12B of the '225 patent illustrates the effect when the inner catheter body is pushed axially by a load in the distal direction in the absence of the lateral support tube 50. As shown, this applies a moment to the end of the column causing it to bend.

Figures 13A, 13B, 13C:
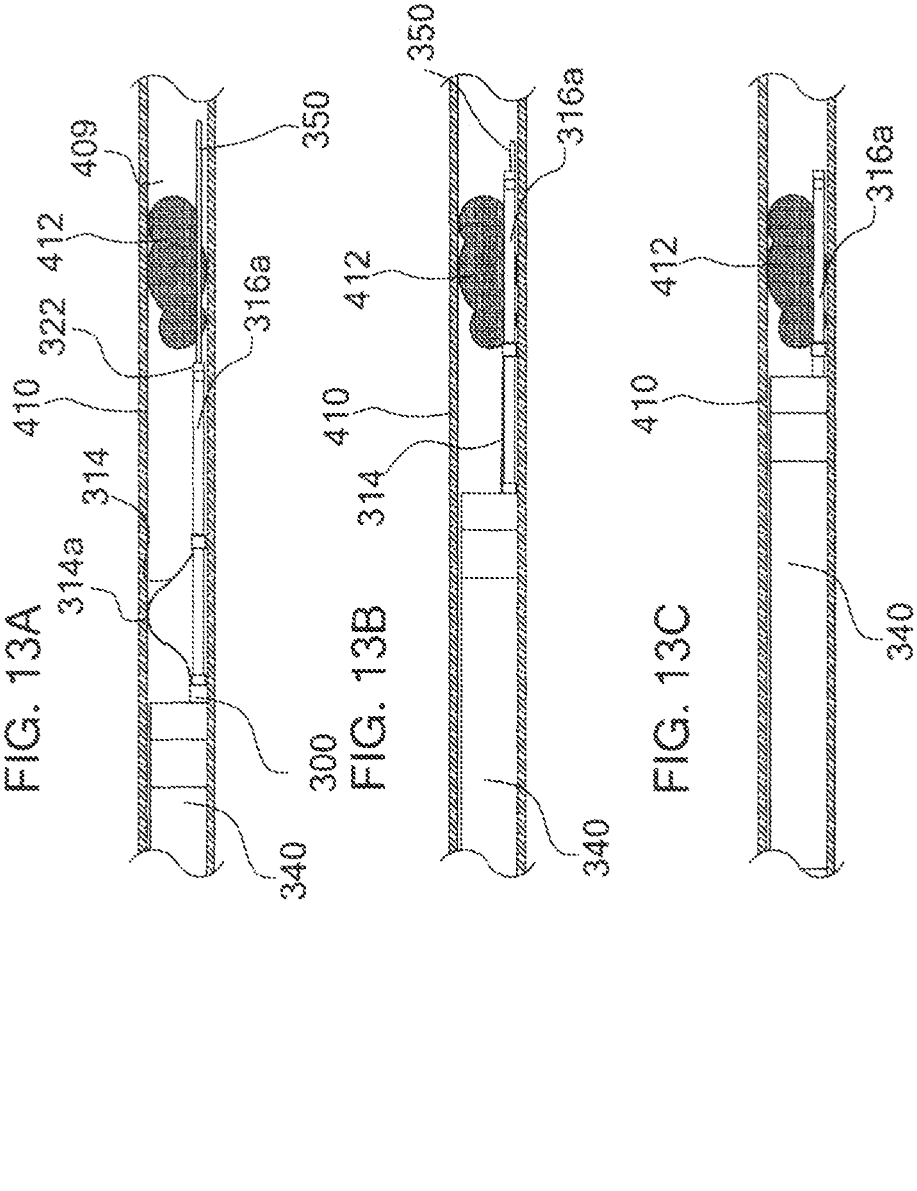

FIGS. 13A and 13C of the '225 patent illustrate the distal deflectable tip under an axial pull load when lateral reinforcement (support) tube 50 is provided. With lateral support tube 50 in place and an axial pull load applied, column 140 can no longer axially compress due to the reinforcement of the column by tube 50. As a result, the entire distal tip, including main (guidewire) lumen, deflects.

Figures 13D, 13E, 13F:
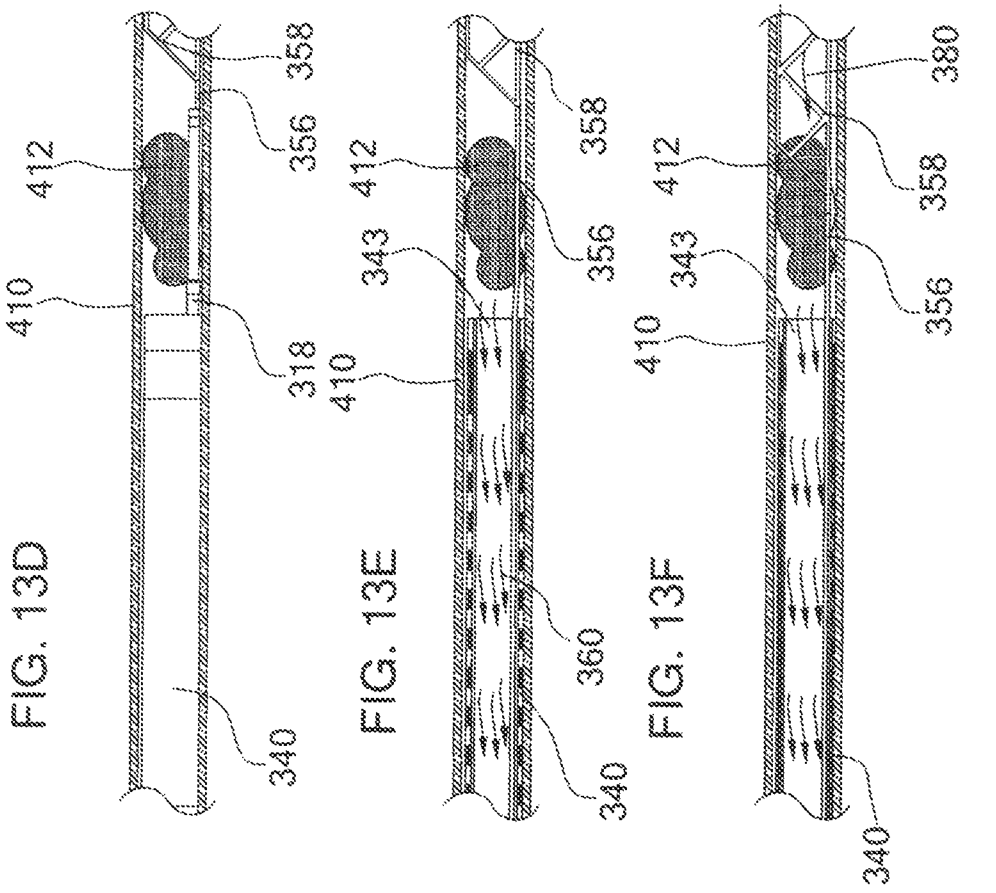

FIGS. 13B and 13D of the '225 patent illustrate the effect when the inner catheter body is moved axially by a load 155 in the distal direction when lateral support tube 50 is provided. This bends the distal tip as in FIG. 12B.

The '225 patent explains that shown in FIGS. 12A-13D is movement of the inner catheter, proximally or distally, respectively, and the same effect can be achieved by movement distally or proximally, respectively, of the outer catheter or by movement of both the inner and outer catheters in the desired directions.

The deflection of the catheter via the column member is described in the '225 patent as follows. Bi-directional deflection of the distal tip of a coaxial microcatheter can be broken down into two distinct motions: axial pull deflection and axial push deflection. Axial pull deflection can be modeled as an eccentrically loaded column while axial push deflection can be modeled as an eccentrically loaded beam.

With respect to axial pull deflection, when no lateral support tube is present on the distal end of the catheter, the column member is modeled as an unsupported eccentrically loaded column. This means that when the inner catheter is moved axially proximally with a force in the proximal direction, the distal end of the column (rectangular nitinol wire) will want to move axially toward its proximal end, resulting in compression (buckling) of the column. With the lateral support tube provided, when the inner catheter is pulled axially with a force in the proximal direction, the column will attempt to compress (buckle) axially, however, it will be restricted by the lateral reinforcement tube 50. Since the tip can no longer fail axially (in compression), it will fail laterally (deflect).

With respect to axial push deflection, when no lateral support tube is present on the distal end of the catheter, the column member is modeled as an eccentrically loaded beam. This means that when the inner shaft is pushed axially with a force it will apply a moment to the end of the beam (e.g., rectangular nitinol wire), which causes it to bend.

Axial pushing and pulling as explained in the '225 patent can be considered in terms of an x-y axis. Axial pushing and pulling will happen on the x axis and bending (deflection) will end up at a point (x,y). So for compression of the column, causing the tip to bend to y1 position, the distal end of the tip is traveling in the −x1 direction towards its proximal end (−x2).

Deflection of the distal tip is achieved by an axial motion, rather than a pulling down on the distal tip so that the bending is achieved not by pulling in the direction of bending but by an axial movement.

In the devices disclosed in the '225 patent, the reinforcement member (support tube) is positioned over the column member and is part of the deflectable catheter as it is attached thereto. In the present invention of FIGS. 6 and 8-11, the device (catheter) is placed within an outer catheter, such as an aspiration catheter, and the deflection mechanism, i.e., the column member, is used to deflect the outer catheter, the wall of the outer catheter acting as the reinforcement/movement restriction member/support tube which effects deflection in the same manner as support tube 50 effects deflection. Thus, the restriction member is not part of the device (catheter) and the device of the present invention can be used to deflect other independent catheters into which it is inserted.

Figures 6, 7:
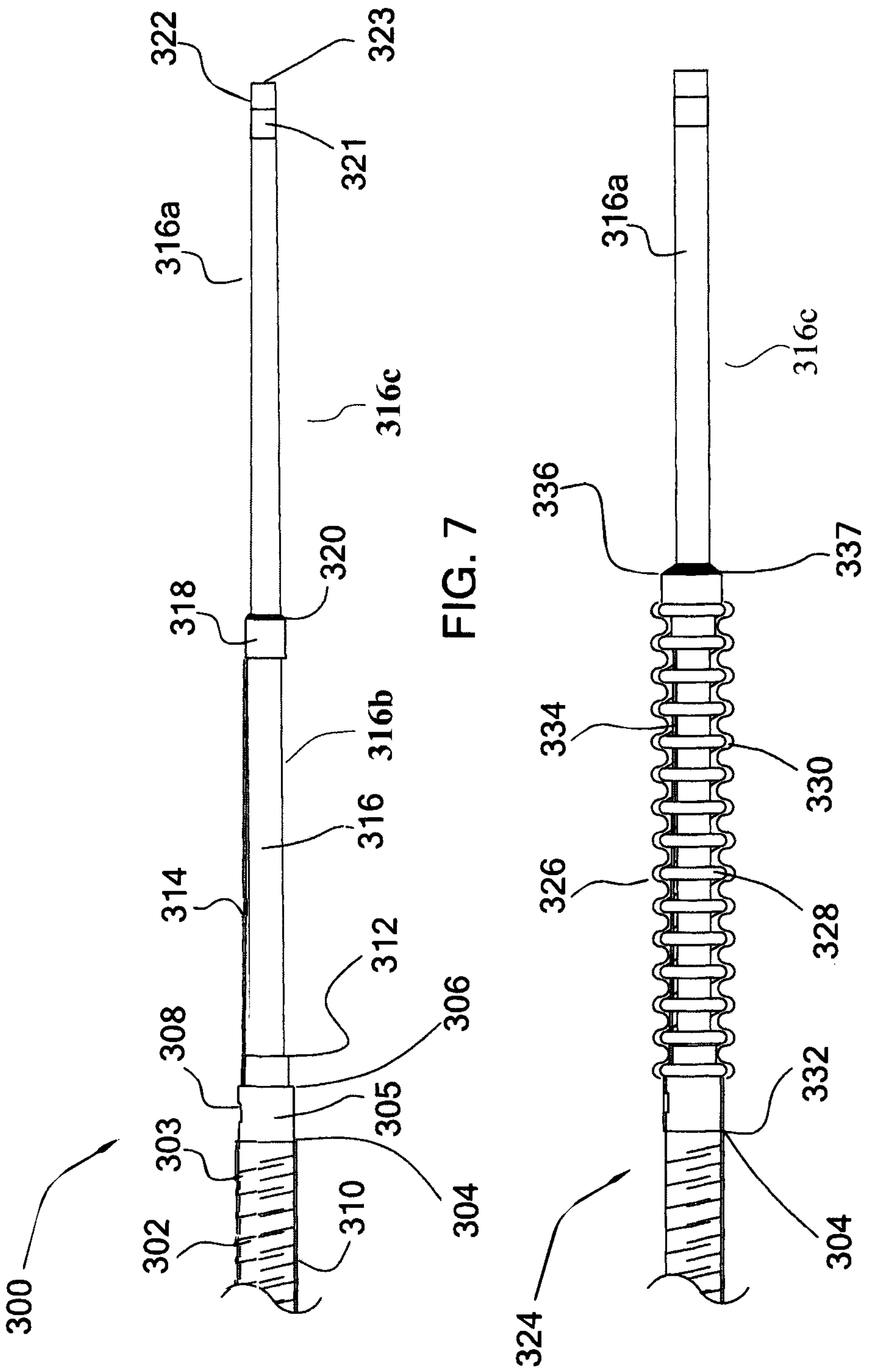
FIG. 6 is a side view of a distal region of the deflectable device for deflecting an outer catheter in accordance with an embodiment of the present invention.
FIG. 7 is a side view of a distal region of an alternate embodiment of the deflectable device of the present invention having a lateral support tube.

FIG. 6 illustrates one embodiment of a bi-directional microcatheter (device) of the present invention with a deflectable tip. The distal section of the catheter 300 is shown in FIG. 6 and includes an outer catheter 302 (also referred to herein as the outer member 302) and an inner catheter 316 (also referred to herein as the inner member 316) positioned within a lumen of the outer catheter 302 and extending distally therefrom so that it has an exposed distal end 316*a* extending distally of a distalmost edge of the outer catheter 302. The exposed distal end 316*a* can range for example from a minimum of 1 cm to greater than 5 cm, although other exposed lengths are also contemplated. This distal extension places the column member distal of the outer catheter while still placing the column member a sufficient distance from the distal end of the inner catheter 316 as discussed below.

The outer catheter (member) 302 in this embodiment is a laser cut stainless steel tube 303 having a non-laser cut section 305 at a distal end 306 with a laser cut side hole 308. Other outer catheter structures can also be utilized such as those described in the '225 patent. Reference numeral 304 of FIG. 6 designates where the laser cut section ends and the non-laser cut section begins. The outer catheter 302 is formed of a tube 303 which is covered with a polymer 310 that preferably covers the entire length of the laser cut tube up to end 304, leaving the non-laser cut section 305 of the tube exposed (uncovered). An inner PTFE liner (not shown) extends the length of tube 303 up to end 304. This leaves the portion of tube 303 under the non-laser cut section 305 free of the PTFE liner.

Inserted partially into the opening in the distal end 306 of tube 303 is marker band 312 which can be welded, soldered, glued (or otherwise attached) in place using hole 308 if needed. The marker band 312 can be inserted into tube 303 up to distal end 304 at which point it will bump into the PTFE liner. The liner thus acts as a proximal stop for inner liner insertion. Sitting (positioned) on top of marker band 312 is a column or column member 314 which is inserted at a proximal end into tube 303 up to a point near distal end 304. The column 314 can be welded, soldered, glued or otherwise attached at its proximal end to the tube 303 either using hole 308 or to the non-laser cut section 305. Column member 314 can be circular or non-circular in cross section. Column member 314 can be of various forms such as a wire or tube.

Inner catheter (member) 316 is positioned within outer catheter tube 303, and during manufacture is inserted through a distal opening in marker band 312 with its exposed distal end region (section) 316*a* extending distally of marker band 312. Inner catheter 316 includes lumen 323, terminating at a distal end of the catheter 316. The exposed distal end region 316*a* has two portions: a more proximal region 316*b* over which the column 314 extends and a more distal region 316*c* which is free of the column 314. These regions are proportioned dependent on the terminal end of the column member. For example, the column member can have a length of about 1.5 cm. Other column lengths are also contemplated. The length of section 316*c* would depend on where the outer member with attached column member sits on distal end region 316*a*, i.e., the length of the column 314. By way of example, if distal region 316*a* is 20 cm in length, and the column 314 is 1.5 cm in length, the column 314 would be 18.5 cm from the distal end so region 316*c* would be 18.5 cm. Other lengths for sections 316*a*, 316*b*, 316*c*, and for column 314, are contemplated. In the embodiment of FIG. 7, by way of example, the column member ends distally at less than the half way mark of distal section 316*a* exposed from outer member 302. The distal region 316*c* length, which has a reduced transverse dimension compared to region 316*b* which has the column member, is designed for passage through blood clots as described below, although other lengths are also contemplated. The inner catheter 316 can be constructed using methods such as described in the '225 patent or other methods. Also, the inner catheter is just one example of an inner catheter that can be used, as other inner catheter structures, such as those described in the '225 patent can be utilized. Such structures however, would need to be modified to accommodate the novel and advantageous column structure and positioning of the present invention.

The inner catheter 316 of FIG. 6 has a variable stiffness design employing an inner PTFE liner, a proximal braid, which sits on the PTFE liner, and an outer coating of polymer of different durometers which soften distally such that distal sections are softer than proximal sections. At the very distal end of inner catheter 316 is a platinum marker band 321 covered with a soft distal tip. The inner catheter 316, can have a non-varying (constant) outer diameter, or alternatively, may taper along its length from proximal to distal up to marker band 318 at which point the diameter will reduce and become constant for a minimum length of preferably at least 1 mm and a maximum length of preferably greater than 5 cm, although other lengths are also contemplated.

Exposed distal end 316*a* preferably has the same flexibility throughout, e.g., the flexibility of section 316*c* is preferably equal to the flexibility of region 316*b*. In this manner, the column member 314 can be positioned i.e., terminate distally, anywhere along the length of this softer region, dependent upon the desired length of the reduced profile portion 316*c* for clot crossing. This soft distal 316*a* section can range from about 15 cm to about 20 cm, although other lengths are also contemplated. Proximal of the soft distal section, the inner catheter has an increased stiffness. This increased stiffness can start just proximal of distal section 316*a* or start further proximal. In preferred embodiments, the column member sits only in the softer distal region 316*a* and does not sit in the stiffer more proximal region of the inner catheter 316.

Marker band 318 is positioned on inner catheter 316 and which marks the distal end of the proximal section 316*b* of exposed distal section 316*b*. Underneath marker band 318 is the distal terminal end of column (column member) 314. The column 314 can be welded, soldered or glued in place, or attached by other methods at its distal end to the marker band 318 and/or outer surface of inner catheter 316. At the distal end of marker band 318 is glue joint 320 to attach the marker band 318 to distal section 316*a*. Marker band 318 can be considered a demarcation of the proximal region 316*b* (with column member) and distal region 316*c* (without column member) of exposed distal section 316*a*. Marker band 321, positioned at the distal end 322 of the catheter 316, is distal of marker band 318; marker band 318 is distal of marker band 312 attached to outer catheter 302. Note that although the column 314 is shown under marker band 318, it can also sit on top of the marker band 318 and can be welded, glued or soldered in place. The marker band 318 can also have a cover (not shown) that covers the entire marker band and is equal to or greater than the outer diameter of outer catheter 302. Likewise, for this particular embodiment, the proximal end of the column 314 may be attached to the marker band 312 and/or the outer catheter 302 using soldering, welding, gluing or other form of mechanical attachment. Thus, the column member 314 is attached at a proximal end to the outer catheter 302 and at a distal end to inner catheter 316.

As shown, the inner catheter 316 extends distally of the column 314. That is, the column 314 has a distal terminal end attached to the inner catheter 316, such as via the marker band 318 described above, wherein the distal terminal end terminates proximally of the distalmost edge of the inner catheter 316. In this manner, an elongated longitudinally extending portion of the inner catheter 316 (referred to as distal region 316*c*) extends distally of the column 314 so that it does not have the column 314 extending therealong. In some embodiments, by way of example, the inner catheter 316 which has sections of variable stiffness can have a length from about 15 cm to about 20 cm. The marker band 318 is utilized for attachment of the column 314 and is spaced from the distalmost edge of the inner catheter 316. The length/spacing (with exposed distal section 316*c*) can be designed/varied for crossing different sized clots. Thus, the system of the outer catheter marker band 308, marker band 318 and column member 314 can be positioned with respect to the inner catheter other than that shown in FIG. 6 to provide different lengths of section 316*c* (devoid of the column).

The inner catheter 316 has a softer distal region than a proximal region, and this softer region includes at least distal region (section) 316*a*. In this manner the region 316*b* (adjacent) which the column 314 extends and the elongated region 316*c* devoid of column 314 are in the softer region of the inner catheter 316*a*. Stated another way, the proximal end and distal terminal end of the column 314 are adjacent the softer distal region of the inner catheter. Regions proximal of this softer (more flexible) region are stiffer and likely would not deflect. That is, the inner catheter has a soft distal section which can be for example about 15 cm to about 20 cm and the column member can sit on any part of it (but remain distal of the next more proximal section of the catheter which is stiffer). In some embodiments, distal region 316*c* can be softer than region 316*b*.

FIG. 7 illustrates another alternate embodiment of a distal portion 324 of a bi-directional microcatheter with a deflectable tip. The construction is the same as distal section 300 of the catheter of FIG. 6 with the exception of the lateral support tube 326 which covers column (column member) 334 and is proximal of the distal region 316*c* of exposed distal section 316*a*. The lateral support tube 326 is composed of a stainless-steel coil 328 and covered with a dip coated silicone 330 having a proximal end 332 which butts up against end 304 and a distal end 336 with glue joint 337 at the distal end of support tube 326. A proximal glue joint (not shown) will attach support tube 326 to the outer catheter. The support tube 326 can act as a reinforcement/restriction member for the column 314. Although this embodiment has a built in movement restriction tube so it does not have the advantage of using an independent catheter as a reinforcement/restriction member, the proximal spacing of the column 314 from the distal end of the inner catheter has the advantages of clot crossing and deflection of the independent catheter as described in the method of use below.

Figures 8, 9:
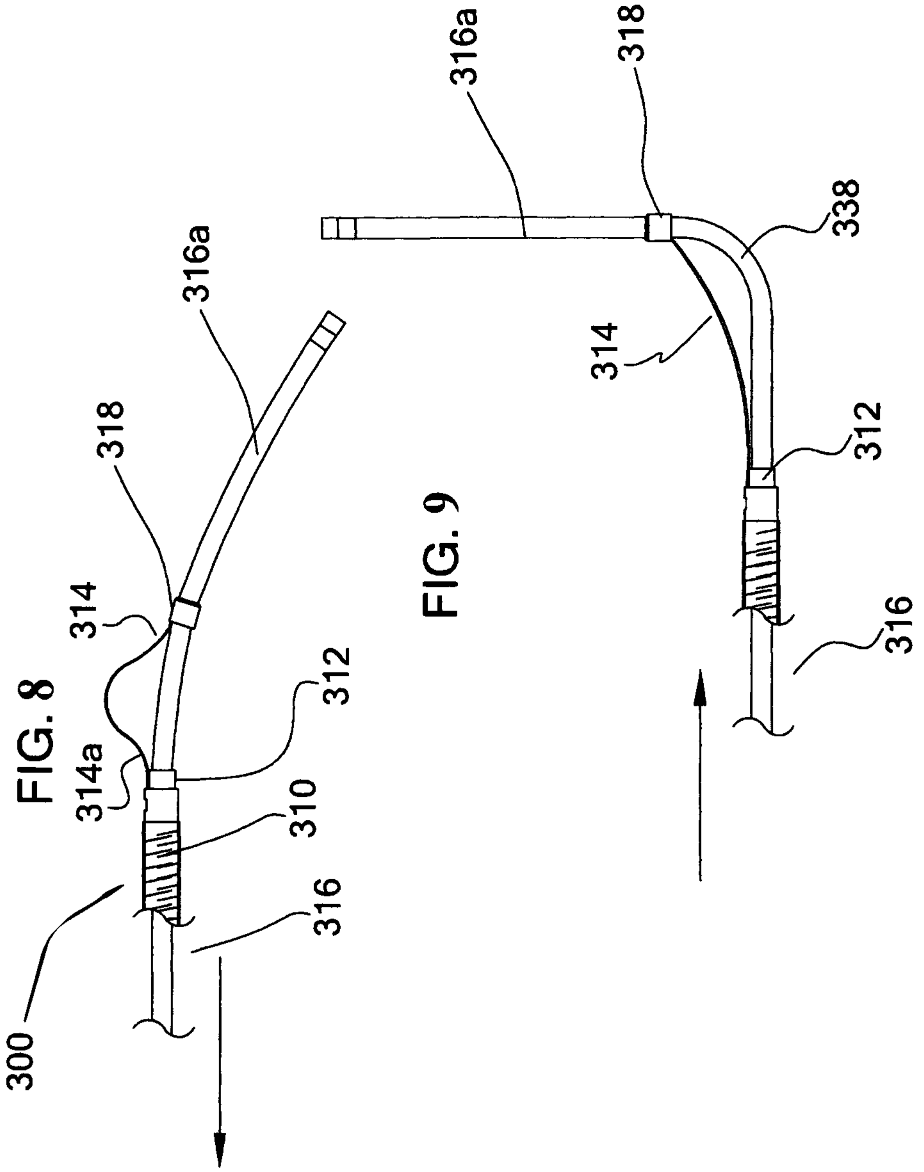
FIG. 8 shows deflection of the device of FIG. 6 when the inner member is pulled proximally relative to the outer member.
FIG. 9 shows deflection of the catheter of FIG. 6 when the inner member is moved distally relative to the outer member.

The use of the deflectable microcatheter 300 of FIG. 6 is shown is FIGS. 8 and 9. When inner catheter 316 is pulled back relative to outer catheter 302, or the outer catheter 302 is pushed forward relative to inner catheter 316, (or movement of the inner catheter 316 and outer catheter 302 in the desired opposing directions) column 314 will want to buckle or compress at region 314*a* causing exposed distal tip 316*a* to move in a downward motion (in a direction away from the bend of the column 314). When the inner catheter 316 is pushed relative to outer catheter 302, or the outer catheter 302 is pulled back relative to inner catheter 316 (or movement of the inner catheter 316 and outer catheter 302 in the desired opposing directions), column 314 attached to the inner catheter 316 will start to bend around region 338 and the exposed distal end 316*a* will move upward (in a direction toward the bend of the column 314). Note region 316*c* will bend and at least a portion of region 316*b* could also bend.

Figures 10, 11:
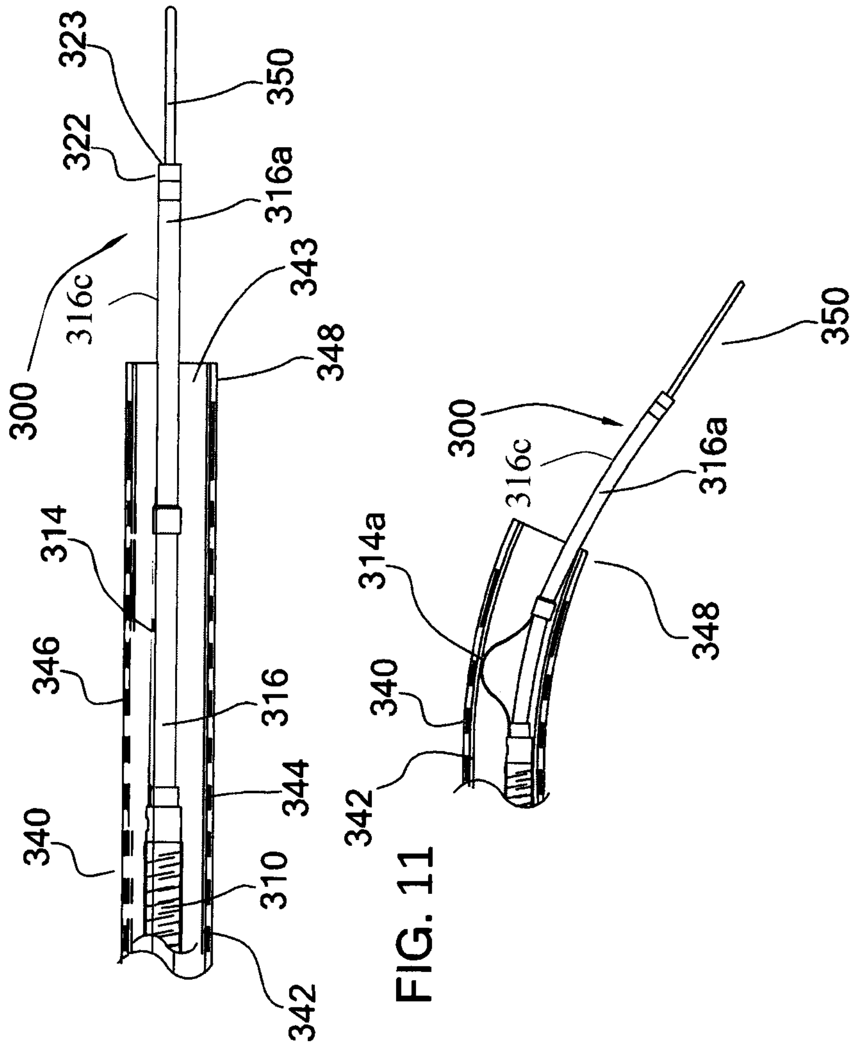
FIG. 10 is a side view of the device of FIG. 6 inserted into an aspiration catheter.
FIG. 11 illustrates deflection of the device and aspiration catheter of FIG. 10 with the aspiration catheter acting as a support tube for deflection.

FIG. 10 illustrates the distal portion 300 of the bi-directional microcatheter of FIG. 6 removably inserted inside an independent outer catheter in the form of aspiration catheter 340. In this system, aspiration catheter 340 acts as a lateral support tube.

Aspiration catheter 340 has an inner lumen 343 and a distal end 348 with a distal opening. The distal portion of the microcatheter 300 is positioned so that column 314 is within the lumen 343 of the aspiration catheter 340 and exposed distal region 316*c* of distal segment 316*a* extends distally of distal end 348 of the aspiration catheter 340 so that at least a portion, and preferably at least 50% of distal region 316*b*, is exposed from aspiration catheter 300. (In some embodiments, this would mean at least 1 cm, or alternatively at least 2 cm, of the distal region, although outer lengths are also contemplated). Positioning the exposed distal region 316*a* in this manner allows the aspiration catheter 340 to act as the lateral support tube to restrict movement of column 314. That is, the aspiration catheter acts as the reinforcement member during axial pull deflection and axial push deflection in a manner as described above with respect to the built in support tube 50. Thus, the column member 314 of the present invention need not be provided with a support tube thereover as part of (built into) the catheter 300 but can use a separate (independent) catheter in which it is inserted to restrict movement of the column member to achieve deflection as described herein. Note that this is achieved since the column 314 is within the confines of a distal portion of the aspiration catheter 340.

In some embodiments, the catheter does not have a reduced profile longitudinally extending section so the column terminates distally adjacent the distal edge of the inner member, but the catheter does not include a reinforcement tube and relies instead on an aspiration or other outer catheter in which it is inserted to act as a reinforcement member for deflection.

The inner lumen of aspiration catheters used to treat stroke tends to be large bore and can vary from less than 0.030" to greater than 0.088". Aspiration catheter 340 is generally constructed like a microcatheter with a PTFE liner 342, a reinforcement structure 344, and a polymer covering 346. The reinforcement structure 344 can be a braid, coil, laser cut tube or a combination of structures. The polymer covering 346 can be a variety of durometers which soften progressively towards the distal end. Note that this is one type of construction for the aspiration catheter and other variations of the construction of aspiration catheter are also contemplated. In addition, this is just a single example of the column member 314 being inserted into an off the shelf device or an independent device to make that device deflectable. This concept can be applied to other catheters and devices that may not be covered under the general term aspiration, e.g., the inner catheter with the attached column member 314 can be inserted into other catheters or tubular members to effect deflection in the manners described herein as the catheter or tube acts as the reinforcement member for the column member 314.

FIG. 11 illustrates distal portion 300 of the bi-directional microcatheter being deflected as shown in FIG. 8. However, the column 314 is now within the aspiration catheter 340. When column 314 at region 314*a* makes contact with PTFE liner 342 of the outer aspiration catheter (or directly with the inner wall of the outer aspiration catheter in embodiments without the inner liner), aspiration catheter 340 will deflect as shown. This may also result in the deflection of the exposed distal section 316*a* of the inner catheter 316 as well as the guidewire 350 extending through the lumen of the inner catheter 316. Note, due to the large variation in possible inner diameters and stiffnesses of aspiration catheter designs, the overall dimensions of the bi-directional catheter including column 314 may differ as aspiration catheters increase in bore size.

The advantage of the deflectable catheter 300 with column member 314 when used with an aspiration catheter (or other independent catheter) can be understood with reference to FIGS. 12A and 12B. The purpose of the aspiration catheter 340 is to revascularize patients suffering from ischemic stroke. One of the challenges in treating stroke is the tortuous anatomy of the neurovasculature. FIG. 12A illustrates a portion of the neuro anatomy 400 consisting of the Internal Carotid (Cavernous) 402, ophthalmic artery 404, and the posterior communicating artery 406. Navigating this portion of the anatomy presents an issue for larger lumen catheters that tend to get caught up at the ophthalmic artery junction 408 in what is called the ledge effect. As shown in FIG. 12A, aspiration catheter 340 fails to follow guidewire 350 due to the large lumen relative to the small wire.

To overcome this, companies introduced distal access catheters or distal assist catheters which are smaller catheters that are placed in the larger bore aspiration catheters. In this set-up, as shown in FIG. 12B, the coaxial system allows the aspiration catheter 340 to be guided by the smaller distal access catheter 352 over the guidewire 350. However, there is still a shoulder 354 between the catheters that can damage the vessel wall and possibly cause a dissection and subarachnoid hemorrhage.

In addition to distal assess or assist catheters, companies have introduced larger guidewires and tapering microcatheters as possible solutions. The problem with these designs is they lack the ability to truly re-direct the entire aspiration catheter tip. This problem is solved by inserting any of the above-described embodiments of the bi-directional microcatheter into the lumen of an aspiration catheter. With the bi-directional catheter of the present invention, the user will be allowed to both manipulate the guidewire as well as to re-direct the aspiration catheter tip.

In addition to the use of aspiration catheters to treat stroke, interventional neuroradiologists sometimes use other clot retrieval tools such as stentrievers. These devices are sometimes used in combination with an aspiration catheter, however, they require a smaller inner/outer diameter catheter for delivery and crossing the clot for deployment. Since crossing the clot should be done with as small a catheter as possible, companies have introduced tapered distal assist catheters as mentioned above. While these designs will provide a smaller distal profile for crossing, they still have the small shoulder problem with a coaxial system as described above. The use of the bi-directional catheter of the present invention with exposed distal tip allows for a low crossing profile as well as full aspiration tip and guidewire control.

Figure 12D:
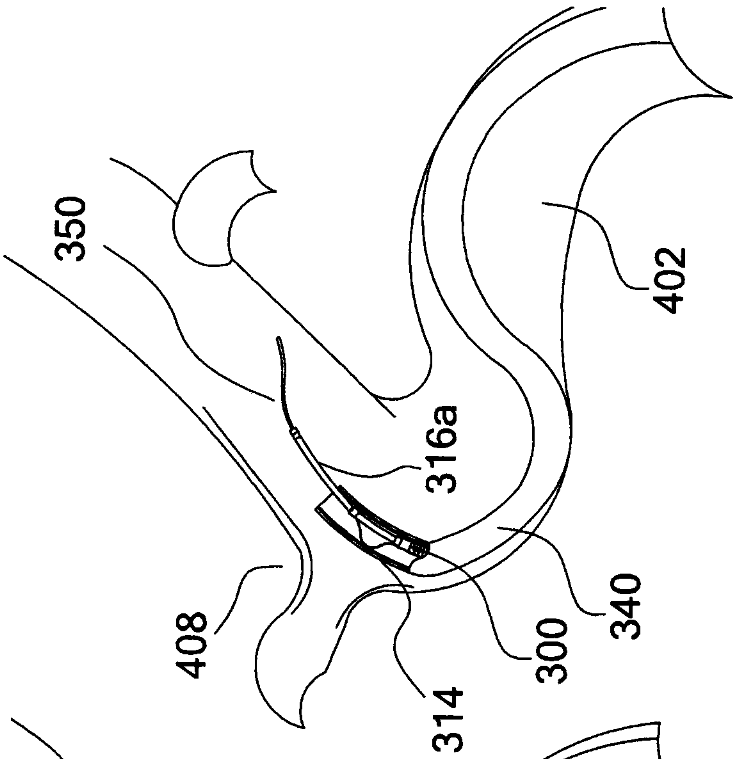
FIGS. 12C and 12D illustrate use of the device of FIG. 6 of the present invention to deflect the aspiration catheter within the neurovasculature.
Figure 12C:
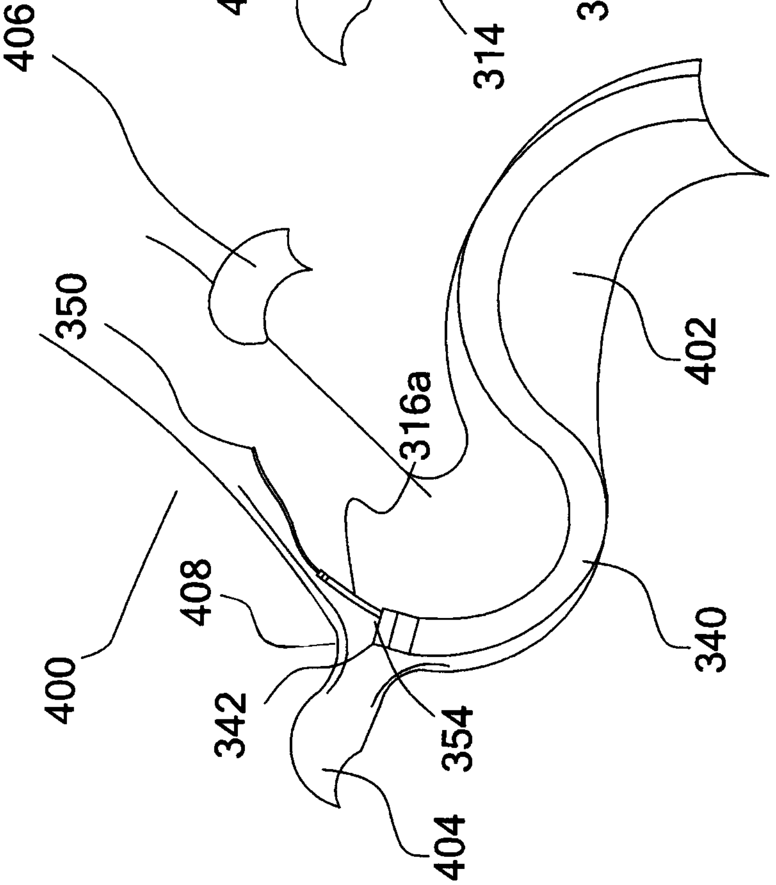

FIGS. 12C and 12D illustrate a bi-directional microcatheter with the distal section inside an aspiration catheter 340 and delivered over a guidewire 350. As shown in FIG. 12C, there exists a shoulder 354 between the microcatheter distal section 300 and the aspiration catheter 340 due to the size discrepancy. If left unaided, the system would possibly come in contact with the ophthalmic artery junction 408 in a similar manner as in FIG. 12A. However, as shown in FIG. 12D, manipulation of the distal end of the bi-directional catheter via the column member 314 of the present invention results in the distal end 348 of aspiration catheter 340 being re-directed away from junction 408 towards the center of the artery. Note the distal section may also have a larger diameter to minimize shoulder 354 that transitions to a smaller diameter 316*a* for crossing clot.

Once the coaxial aspiration system reaches the clot, the initial step will be to cross the clot to place the stentriever for clot removal. FIGS. 13A-13F show the general steps for treatment. FIG. 13A illustrates crossing of the clot 412 in vessel 409, having inner vessel wall 410, first with the guidewire 350. For this step, the column 314 may be used to stabilize the distal exposed section 316*a* by moving the inner catheter 316 (not shown) until region 314*a* of column 314 comes in contact with wall 410. Once the guidewire 350 has crossed the clot 412, the column 314 is flattened and the exposed distal region 316*c* of exposed distal end 316*a* is pushed forward, through clot 412 as shown in FIG. 13B. The guidewire 350 is then removed as in FIG. 13C and stentriever 358 with delivery wire 356 is deployed as shown in FIG. 13D. The bi-directional microcatheter is then removed and aspiration (see arrows 360) is effected through the inner lumen 343 of aspiration catheter 340 as shown in FIG. 13E. Under aspiration, the stentriever 358 is then pulled into the clot (see arrow 380) using delivery wire 356 and the entire coaxial system is pulled together as shown in FIG. 13F to dislodge and remove the clot and remove it from the body. It should be noted that the steps of FIGS. 13A-13F for clot removal is just one example as fewer or more steps can be utilized using the deflectable inner catheter/column member of the present invention for improved access. As can be appreciated, the lower profile distal section 316*c* of exposed distal region 316*a* of the inner catheter 316, due to the absence of column 314, facilitates crossing of the clot.

In summary, in accordance with one method of the present invention, the following method for directing a catheter through the vasculature is provided comprising: inserting a first device into an outer catheter, the first device having an inner member, an outer member and a column member connected to the inner member and/or outer member; moving one of the inner member or outer member with respect to the other to effect axial compression of the column member as the column member is bent within a lumen of the outer catheter, the inner wall restricting movement of the column member so a distal portion of the inner member deflects laterally; and advancing the outer catheter either independent of, or together with, the device, over the deflected distal portion to redirect the outer catheter.

Note the catheters of the present invention can be used to deflect a variety of other devices or tubular members and is not limited to aspiration catheters.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the above description, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design.

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A system comprising:

a) a first device having i) an outer member having a proximal portion and a distal portion;

ii) an inner member positioned coaxially within the outer member, the inner member extending distally of the outer member and having a distal portion;

iii) an elongated column member attached to the inner member and extending external of the inner member; and b) an independent outer catheter having a lumen, the outer member and inner member of the first device removably insertable into and slidably positioned within the lumen of the outer catheter during use so that the column member is positioned in the lumen of the outer catheter and a distal portion of the inner member extends distally of the lumen in the outer catheter;

c) wherein when one of the inner member or outer member is moved with respect to the other, axial compression of the column member is restricted by an inner wall of the outer catheter causing the distal portion of the inner member to deflect laterally to redirect the outer catheter.

2. The system of claim 1, wherein the inner member has a central longitudinal axis and the column member is radially offset with respect to the central longitudinal axis.

3. The system of claim 1, wherein the outer catheter is an aspiration catheter.

4. The system of claim 1, wherein the column member is non-circular in cross-section.

5. The system of claim 1, further comprising a marker band positioned on the inner member and the column member is attached to the marker band.

6. The system of claim 1, wherein the column member is attached at a proximal end to the outer member and at the distal end to the inner member.

7. The system of claim 1, wherein the column member has a distal terminal end and the inner member extends for a length from about 2 cm from the terminal end of the column member.

8. The system of claim 7, wherein the distal terminal end is adjacent a softer distal section of the inner member.

9. The system of claim 1, wherein the column member has a reinforcement member positioned thereover, the reinforcement member coming into contact with the inner wall of the outer catheter during deflection.

10. The system of claim 1, wherein the column member comes into contact with the inner wall of the outer catheter during deflection.

11. A system comprising:

a) an outer member having a proximal portion and a distal portion;

b) an inner member positioned coaxially within the outer member, the inner member having an elongated exposed distal region extending distally of the outer member and having a distalmost edge, the inner member having a distal section softer than a more proximal section; and c) an elongated column member attached to the inner member and extending external of the inner member adjacent the softer distal section, the column member attached at a first end to the outer member and at a second end to the inner member and having an elongated uncovered exposed portion, the second end of the column member positioned proximally of the distalmost edge to leave an extended elongated portion of the distal region of the inner member extending distally of the column member free of the column member, and the second end of the column member terminating adjacent the softer distal section of the inner member;

d) wherein when one of the inner member or outer member is moved with respect to the other, the distal portion of the inner member deflects laterally;

e) wherein lateral deflection is effected when the column member is restricted by an inner wall of an independent outer catheter in which the column member is positioned.

12. The system of claim 11, further comprising a marker band positioned on the inner member, and the column member is attached to the marker band.

13. The system of claim 11, wherein the inner member has a central longitudinal axis and the column member is radially offset with respect to the central longitudinal axis.

14. The system of claim 11, wherein the outer catheter is an aspiration catheter.

15. The system of claim 11, wherein the column member is non-circular in cross-section.

* * * * *